(12) United States Patent
Willhite et al.

(10) Patent No.: US 11,189,979 B2
(45) Date of Patent: Nov. 30, 2021

(54) POWER PACK

(71) Applicant: Gyrus ACMI, Inc., Southborough, MA (US)

(72) Inventors: Joel A. Willhite, Memphis, TN (US); David C. Church, Millington, TN (US); Rodney Loyd, Arlington, TN (US)

(73) Assignee: Gyrus Acmi, Inc., Westborough, MA (US)

( * ) Notice: Subject to any disclaimer, the term of this patent is extended or adjusted under 35 U.S.C. 154(b) by 54 days.

(21) Appl. No.: 16/016,796

(22) Filed: Jun. 25, 2018

(65) Prior Publication Data

US 2019/0393660 A1 Dec. 26, 2019

(51) Int. Cl.
| | |
|---|---|
| *H01R 33/90* | (2006.01) |
| *H02M 7/00* | (2006.01) |
| *H05K 5/00* | (2006.01) |
| *A61B 17/3207* | (2006.01) |
| *A61B 18/12* | (2006.01) |
| *A61B 17/24* | (2006.01) |
| *A61B 18/00* | (2006.01) |
| *A61B 17/32* | (2006.01) |

(52) U.S. Cl.
CPC ............. *H01R 33/90* (2013.01); *A61B 17/24* (2013.01); *A61B 17/320758* (2013.01); *A61B 18/1206* (2013.01); *H02M 7/003* (2013.01); *H05K 5/0017* (2013.01); *A61B 2017/246* (2013.01); *A61B 2017/320004* (2013.01); *A61B 2018/00178* (2013.01); *A61B 2018/00327* (2013.01); *H01R 2201/12* (2013.01)

(58) Field of Classification Search
CPC ............. A61B 17/24; A61B 17/320758; A61B 18/1206; A61B 2017/246; A61B 2017/320004; H02M 7/003; H05K 5/0017
See application file for complete search history.

(56) References Cited

U.S. PATENT DOCUMENTS

| | | | | |
|---|---|---|---|---|
| 6,017,354 A | * | 1/2000 | Culp | ................. A61B 17/1626 604/22 |
| 7,094,231 B1 | * | 8/2006 | Ellman | ............... A61B 18/1206 606/34 |
| 2001/0029315 A1 | * | 10/2001 | Sakurai | .......... A61B 17/320068 600/101 |

* cited by examiner

*Primary Examiner* — Daniel Kessie
(74) *Attorney, Agent, or Firm* — Schwegman Lundberg & Woessner, P.A.

(57) ABSTRACT

Provided is a power pack comprising an AC power connector configured to be connectable to an outside AC power source; a rectification and filtering unit configured to be in electronic communication with the AC power connector; a controlling unit; and a medical device connector configured to be connectable to a medical device, the medical device connector configured to be in electronic communication with the controlling unit, wherein the power pack is configured to be capable of detecting a connection of the medical device with the power pack and also capable of demonstrating the connection through an outside indicator disposed on the exterior of the power pack once the medical device is connected to the power pack through the medical device connector.

16 Claims, 4 Drawing Sheets

POWER PACK

FIELD

The present disclosure relates generally to a power pack. More particularly, the present disclosure relates to a power pack capable of providing consistent and reliable power for many types of surgical devices with different functions.

BACKGROUND

Currently available debriders, shavers and similar devices utilize an expensive and often bulky power console to which the handpiece of a medical device is connected. This provides adequate power, but is often unattractive to consumers in cost-sensitive sites of care due to expense, size in constrained office or clinic areas, and complexity of setup and breakdown during time-constrained procedures and/or where little trained assistance is available. Consequently, there exists a need for better power supplying devices for various types of surgical devices.

SUMMARY

In an embodiment, the present disclosure provides a power pack. In an embodiment, the power pack comprises an AC power connector. In an embodiment, the power pack comprises a rectification and filtering unit. In an embodiment, the power pack comprises a controlling unit. In an embodiment, the power pack comprises a medical device connector. In an embodiment, the power pack comprises a connection signal light. In an embodiment, the power pack comprises a suction console connector. In an embodiment, the power pack comprises a footswitch connector. In an embodiment, the power pack comprises a ground bond testing connector. In an embodiment, the power pack comprises a speed dial. In an embodiment, the power pack comprises a RF energy output connector.

In an embodiment, the present disclosure provides a power pack. In an embodiment, the power pack comprises an AC power connector and a rectification and filtering unit. In an embodiment, the power pack comprises an AC power connector, a rectification and filtering unit, and a controlling unit. In an embodiment, the power pack comprises an AC power connector, a rectification and filtering unit, a controlling unit, and a medical device connector. In an embodiment, the power pack comprises an AC power connector, a rectification and filtering unit, a controlling unit, a medical device connector, and a connection signal light. In an embodiment, the power pack comprises an AC power connector, a rectification and filtering unit, a controlling unit, a medical device connector, a connection signal light, and a suction console connector. In an embodiment, the power pack comprises an AC power connector, a rectification and filtering unit, a controlling unit, a medical device connector, a connection signal light, a suction console connector, and a footswitch connector. In an embodiment, the power pack comprises an AC power connector, a rectification and filtering unit, a controlling unit, a medical device connector, a connection signal light, a suction console connector, a footswitch connector, and a ground bond testing connector.

In an embodiment, the present disclosure provides a power pack. In an embodiment, the power pack comprises an AC power connector, a rectification and filtering unit, a controlling unit, a medical device connector, a suction console connector, a footswitch connector, a ground bond test connector, a connection signal light, and a speed dial. In an embodiment, the power pack comprises an AC power connector, a rectification and filtering unit, a controlling unit, a medical device connector, a suction console connector, a footswitch connector, a ground bond test connector, a connection signal light, and a RF energy connector. In an embodiment, the power pack comprises an AC power connector, a rectification and filtering unit, a controlling unit, a medical device connector, a suction console connector, a footswitch connector, a ground bond test connector, a connection signal light, a speed dial, and a RF energy connector.

In an embodiment, the present disclosure also provides a method of removing nasal polys and/or other sinus or nasal tissues by using a power pack as described herein.

DETAILED DESCRIPTION

Figure 1:
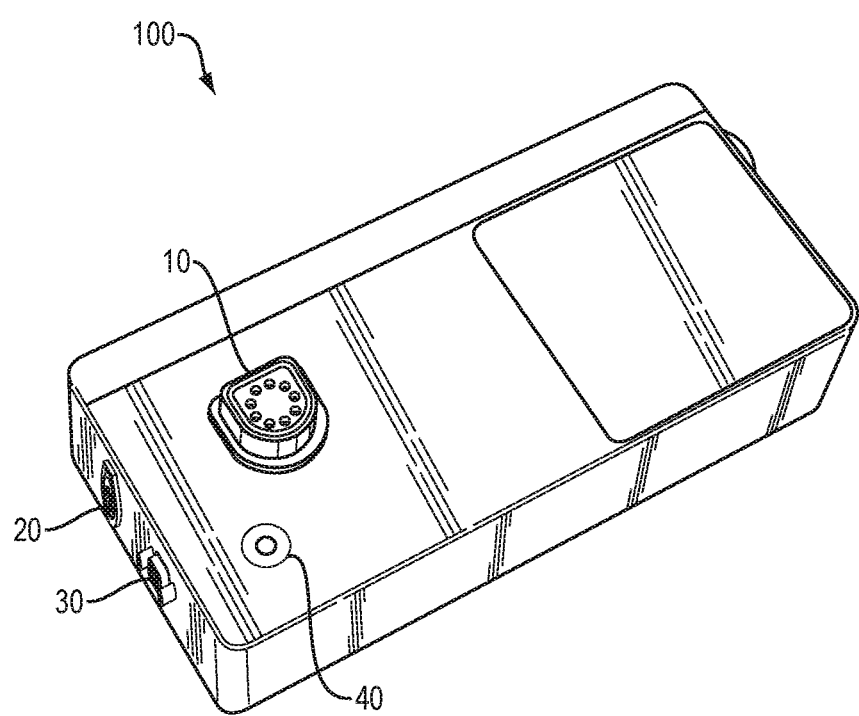
FIG. 1 is a schematic illustration of the exterior of a power pack in accordance with one aspect of the present disclosure.

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

All numeric values are herein assumed to be modified by the term "about" whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. Even more specifically, "about" can be understood as within 10%, 9%, 8%, 7%, 6%, 5%, 4%, 3%, 2%, 1%, 0.5%, 0.1%, 0.05%, or 0.01% of the stated value. Unless otherwise stated, all ranges include both endpoints and all numbers between the endpoints. The use of "about" or "approximately" in connection with a range applies to both ends of the range. Thus, "about 10 to 30" is intended to cover "about 10 to about 30", inclusive of at least the specified endpoints.

In an embodiment, the present disclosure provides a power pack. In an embodiment, the power pack comprises an AC power connector. In an embodiment, the power pack comprises a rectification and filtering unit. In an embodiment, the power pack comprises a controlling unit. In an embodiment, the power pack comprises a medical device connector. In an embodiment, the power pack comprises a connection signal light. In an embodiment, the power pack comprises a suction console connector. In an embodiment, the power pack comprises a footswitch connector. In an embodiment, the power pack comprises a ground bond testing connector. In an embodiment, the power pack comprises a speed dial. In an embodiment, the power pack comprises a RF energy output connector.

In an embodiment, the present disclosure provides a power pack. In an embodiment, the power pack comprises an AC power connector and a rectification and filtering unit. In an embodiment, the power pack comprises an AC power connector, a rectification and filtering unit, and a controlling unit. In an embodiment, the power pack comprises an AC power connector, a rectification and filtering unit, a controlling unit, and a medical device connector. In an embodiment, the power pack comprises an AC power connector, a rectification and filtering unit, a controlling unit, a medical device connector, and a connection signal light. In an embodiment, the power pack comprises an AC power connector, a rectification and filtering unit, a controlling unit, a medical device connector, a connection signal light, and a suction console connector. In an embodiment, the power pack comprises an AC power connector, a rectification and filtering unit, a controlling unit, a medical device connector, a connection signal light, a suction console connector, and a footswitch connector. In an embodiment, the power pack comprises an AC power connector, a rectification and filtering unit, a controlling unit, a medical device connector, a connection signal light, a suction console connector, a footswitch connector, and a ground bond testing connector.

In an embodiment, the present disclosure provides a power pack comprising an AC power connector, a rectification and filtering unit, a controlling unit, a medical device connector, a suction console connector, a footswitch connector, a ground bond test connector, a connection signal light, and a speed dial. In an embodiment, the present disclosure provides a power pack comprising an AC power connector, a rectification unit, a controlling unit, a medical device connector, a suction console connector, a footswitch connector, a ground bond test connector, a connection signal light, and a RF energy connector. In an embodiment, the power pack comprises an AC power connector, a rectification and filtering unit, a controlling unit, a medical device connector, a suction console connector, a footswitch connector, a ground bond test connector, a connection signal light, a speed dial, and a RF energy connector.

In an embodiment, the present disclosure provides a power pack comprising: an AC power connector configured to be connectable to an outside AC power source; a rectification and filtering unit configured to be in electronic communication with the AC power connector; a controlling unit; and a medical device connector configured to be in electronic communication with the controlling unit, wherein the power pack is configured to be capable of detecting a connection of a medical device with the power pack once the medical device is connected to the power pack through the medical device connector. In an embodiment, the power pack also comprises a footswitch connector configured to be in electronic communication with the controlling unit. In an embodiment, the power pack also comprises a suction console connector. In an embodiment, the power pack also comprises a ground bond test connector. In an embodiment, the power pack also comprises a connection signal light. In an embodiment, the power pack also comprises a RF energy connector. In an embodiment, the power pack comprises a housing having an exterior. In an embodiment, the exterior comprises a base and a top.

In an embodiment, the present disclosure provides a power pack comprising: an AC power connector configured to be connectable to an outside AC power source; a rectification and filtering unit configured to be in electronic communication with the AC power connector; a controlling unit; and a medical device connector configured to be in electronic communication with the controlling unit, wherein the controlling unit is configured to be capable of detecting a connection of a medical device with the power pack once the medical device is connected to the power pack through the medical device connector. In an embodiment, the controlling unit is configured to be capable of generating and demonstrating a connection signal through a signal light disposed on the power pack. In an embodiment, a single signal light may be used for different power modalities or the type of the medical device through different colors. In an embodiment, one or more signal lights may be disposed on the power pack for different power modalities or the type of the medical device with each signal light indicating one power modality or the type with a specified color.

In an embodiment, the present disclosure provides a power pack comprising: a housing having an exterior; an AC power connector disposed on the housing, the AC power connector configured to be connectable to an outside AC power source; a rectification and filtering unit disposed inside the housing, the rectification and filtering unit configured to be in electronic communication with the AC power connector; a controlling unit disposed inside the housing; and a medical device connector disposed on the housing, the medical device connector configured to be in electronic communication with the controlling unit; wherein the controlling unit is configured to be capable of detecting and indicating a connection of a medical device with the power pack once the medical device is connected to the power pack through the medical device connector by way of a connection signal light disposed on the exterior of the housing.

In an embodiment, the present disclosure provides a power pack comprising: an AC power connector configured to be connectable to an outside AC power source; a rectification and filtering unit configured to be in electronic communication with the AC power connector; a controlling unit; a medical device connector configured to be connectable to a medical device, the medical device connector configured to be in electronic communication with the controlling unit; and a footswitch connector configured to be in electronic communication with the controlling unit, wherein the controlling unit is configured to be capable of detecting a connection once the medical device is connected to the medical device connector.

In an embodiment, the present disclosure provides a power pack comprising: an AC power connector configured to be connectable to an outside AC power source; a rectification and filtering unit configured to be in electronic communication with the AC power connector; a controlling unit; a medical device connector configured to be connectable to a medical device, the medical device connector configured to be in electronic communication with the controlling unit; a footswitch connector configured to be in electronic communication with the controlling unit; and a ground bond test connector configured to be a grounding source, wherein the controlling unit is configured to be capable of detecting a connection once a medical device is connected to the medical device connector.

In an embodiment, the present disclosure provides a power pack comprising: an AC power connector configured to be connectable to an outside AC power source; a rectification and filtering unit configured to be in electronic communication with the AC power connector; a controlling unit; a medical device connector configured to be connectable to a medical device, the medical device connector configured to be in electronic communication with the controlling unit; a footswitch connector configured to be in electronic communication with the controlling unit; a suction console connector; and a ground bond test connector configured to be a grounding source, wherein the controlling unit is configured to be capable of detecting a connection once a medical device is connected to the medical device connector.

In the above embodiments, the power pack is configured to have a medical device connector configured to connect with a medical device. The medical device may be a disposable debrider or shaver such as a disposable tonsil adenoid debrider (DTAD) from Olympus. The medical device may also be an M4, M5, or Nexus device from Medtronic. It may also be Diego® or Diego® Elite device from Olympus. It may also be a Dyonics device from Smith & Nephew. The medical device may be a microdebrider. The medical device may be a reusable debrider. The medical device may be a sinus debrider. The medical device may be a disposable sinus debrider. The medical device may be a reusable shaver. It may be any other suitable medical devices such as disclosed in the U.S. Pat. Nos. 7,226,459, 7,510,563, and 7,666,200, the entire contents of which are all incorporated herein for reference.

In the above embodiments, the medical device comprises a handpiece. The handpiece is configured to have a push button or an activation switch or knob. It should be understood that the handpiece may also be configured to have other types of activation modes such as voice activation or control. The handpiece is configured to be in electronic communication with the power pack, and the electronic communication may be controlled through the push button or the activation switch. After the handpiece is plugged into the power pack, a connection signal is generated and displayed through an LED light or any suitable connection signal indicator. More particularly, controller unit of the power pack is configured to be capable of determining a particular type of handpiece through a cable employed to connect the power pack and the handpiece. More particularly, the cable is configured to utilize a combination of connections or jumpers to particular pins of the cable to represent the particular type of a handpiece. The cable may be configured to be either connected to ground or to a +5 volt. Consequently, the controller unit is capable of identifying the type of the handpiece through identifying specific combinations from the inserted cable from the handpiece.

In the above embodiments, the medical device comprises a handpiece. The handpiece is configured to be connectable with a cutting blade. The cutting blade may comprise a cutting window. It should be understood that the cutting blade may be any type known in the art. In the above embodiments, a rotational motor may be used to couple with a parallel gear train to impart oscillatory motion for the cutting blade of the medical device. The medical device may also use a reciprocating mechanism to drive the cutting blade. The medical device may also use both mechanisms described above to rotate and reciprocate the cutting blade. It should be understood that the medical device may also use other types of driving mechanisms known in the art. It should also be understood that the power pack as described herein is configured to differentiate and drive the cutting blade of the medical device regardless of its driving mechanism. The power pack can also be configured to distinguish between different cutting blade types within one type of drive mechanism and can adjust the drive signal to different parameters for each blade type to optimize performance. For example, the power pack may be configured to adjust blade reciprocation frequency or drive pulse width. In some preferred embodiments, the handpiece may comprise a solenoid. The solenoid is configured to drive or reciprocate the cutting blade. In some preferred embodiments, the blade reciprocation frequency may be in the range of about 1 to about 20 hertz. In some more preferred embodiments, the blade reciprocation frequency may be about 6, 8, or 10 hertz. In some preferred embodiments, the drive pulse width may be in the range of about 5 to 25 milliseconds. In some more preferred embodiments, the drive pulse width may be about 10, 11, 12, 13, 14, 15, 16, 17, 18, 19, or 20 milliseconds. In some preferred embodiments, the drive pulse width may be pulse with modulation (PWM). Additionally, the push button of the handpiece may also be configured to have a toggle function such that one push of the push button opens the cutting window, and a quick second push closes the cutting window.

In the above embodiments, the power pack is configured to have a controlling unit. The controlling unit may be configured to comprise a controller printed circuit board (PCB). The controller PCB may comprise a drive circuit for drive signal delivery to a medical device. The controller PCB may also be configured to have a safety circuit to prevent any unintended operation of the medical device in the event of a microcontroller malfunction or software malfunction. The drive circuit may be a MOSFET circuit. The controller PCB may comprise a microcontroller unit (MCU). The MCU is configured to monitor the system status, to process user inputs, and to generate the drive signals to control the drive circuit. The controller PCB may be configured to receive input from the push button or the activation switch located on the handpiece of a medical device to generate an output to control the operation of the medical device's cutting blade. The input may also come from the footswitch to generate an output either analog i.e. 0-10 volts, 4-20 mA (or other ranges known in the art) or digital on-off to control the motion of the medical device's cutting blade. In the above embodiments, the push button of the handpiece or the footswitch may also be configured such that a momentary press of the button or the footswitch generates a toggle function to open and close the cutting window of the medical device. In the above embodiments, the controller PCB is also configured to monitor and detect when a handpiece of the medical device is connected, and will generate a connection signal for an LED status indicator located on the exterior of the power pack once connected.

In the above embodiments, the power pack is configured to have a controlling unit. Additionally, or alternatively, the controlling unit is configured to be capable of detecting the power modality of the medical device. Also, the controlling unit is configured to be capable of detecting a connection of a handpiece of a medical device with the power pack. For example, the controller unit may be configured to be capable of identifying the handpiece having a 2 mm or 4 mm tubing for the type of the cutting blades of the medical device through the connecting cable. It may also be configured to be capable of identifying other information such as driving mechanism and driving element of the medical device.

In the above embodiments, the power pack is configured to comprise an AC power connector and a rectification and filtering unit. The AC power connector is configured to connect to an outside AC power source. The rectification and filtering unit is configured to be in electronic communication with the AC power connector. The outside AC power source may be from a regular or fixed wall outlet with a voltage in the range of 100V to 240V. The outside AC power source may also be a movable source. The outside AC power source is understood to be the initial power source. The rectification and filtering unit is configured to provide DC power supply for the medical device from the outside AC power source through the AC power connector. It should be understood that the rectification and filtering unit may comprise any additional components that is necessary for the unit to supply DC power in a reliable and desirable way. The additional components may comprise additional filter before and/or after the rectification. The DC power supply may be configured to be available at a voltage of from 12V to 36V. More particularly, it may be configured to be available at a voltage of 12V, 18V, 24V, 28V, or 36V or 48V. More preferably, the DC power supply may be available at a voltage of 24V.

In the above embodiments, the power pack may be configured to comprise a footswitch connector. The footswitch connector is configured to be connectable to a footswitch. The footswitch may be configured to comprise a foot pedal. The footswitch connector is configured to be in electronic communication with the controlling unit of the power pack. It is also configured to be in electronic communication with the medical device connector of the power pack. Actually, a press of the foot pedal of the footswitch should be an equivalent to a depression of the push button of the handpiece of a medical device. Additionally, the foot pedal may also be configured to have a toggle function similar to the toggle function of the push button of the handpiece as described herein. Additionally, the foot pedal may also be configured to have an analog output to vary the speed of the handpiece on top of its on-off functionality.

In the above embodiments, the power pack may be configured to comprise a suction console connector for connection with a suction console. The suction console connector is configured to turn on the suction function of the suction console. The suction console connector may be configured to automatically turn on the suction once it is connected to the suction console. It may also be configured to turn on the suction through a switch or button disposed on the exterior of the power pack. The suction console is understood to provide suction function to facilitate removal of liquid or solid materials produced or used during a surgical operation.

In the above embodiments, the power pack is configured to comprise a ground bond test or testing connector. The ground bond test connector may be connected to a Kelvin test setup to test or safeguard the safety of the power pack and the whole surgical assembly. It should be understood that any other grounding installations may be possible so long as they are made to provide adequate grounding protection and safety for a user.

In the above embodiments, the power pack may also be configured to comprise a RF energy connector. The RF energy connector is configured to be in electronic communication with a RF energy source. The RF energy connector is configured to be connectable to a RF energy source. The RF energy connector may be configured to be in electronic communication with a bipolar RF energy source. The RF energy connector may be configured to be connectable to a bipolar RF energy source. The RF energy connector may be configured to be in electronic communication with a monopolar RF energy source. The RF energy connector may be configured to be connectable to a monopolar RF energy source. Consequently, the power pack as described herein may be used for surgical operations where a RF energy may be necessary or desirable.

In the above embodiments, a speed dial may also be a speed switch with 2 or more discrete settings. The speed dial may be configured to a continuous range of speeds (within a minimum and maximum). The speed dial may be disposed on the exterior of the power pack to control the speed of the cutting blade of a medical device. The speed dial may be configured/installed in a manner known in the art.

In the above embodiments, the medical device connector, the AC outside source connector, the suction console connector, and the ground bond test connector are all preferably disposed on the housing or the exterior of the housing. The universal DC power supply and the controlling unit are preferably disposed inside the housing of the power pack.

In an embodiment, the present disclosure also provides a method of making a power pack as described herein. The method includes making a housing for the power pack. The housing includes a base or bottom portion and a cover or top portion, both may be made of plastic or other suitable materials by injection mold or 3D printing. The method also includes assembling wire harnesses, screwing in place any circuit boards that may be necessary, and plugging the wire harness into the circuit boards. The method further includes tightening and securing the base and the top with screws.

In an embodiment, the present disclosure also provides a method of providing a reliable DC power supply for a surgical operation without using batteries. The method includes providing a power pack as described herein during a surgical operation. In an embodiment, the present disclosure also provides a method of reducing cost for a surgical operation. The method includes using a power pack as described herein since the power pack can be easily and quickly set up with other surgical components for a surgical operation. The use of such a power pack is thus expected to reduce cost for surgical operations. Additionally, the power pack is made to be small, light, and portable. Consequently, the power pack as described herein may be suitable for an office environment, for cost-sensitive regions, and/or for ambulatory surgery centers.

In an embodiment, the present disclosure also provides a method of removing nasal polyps and/or other sinus or nasal tissues by using a power pack as described herein. The method includes providing a medical device capable of cutting or removing sinus or nasal tissues. The method includes connecting the medical device to the power pack as described herein. The method also includes connecting other components that may be necessary to the power pack. The method also includes turning on the medical device to cut/remove nasal polyps or other nasal tissues. The method may be used to treat sinusitis in an office setting by using a power pack as described herein.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

Figure 2:
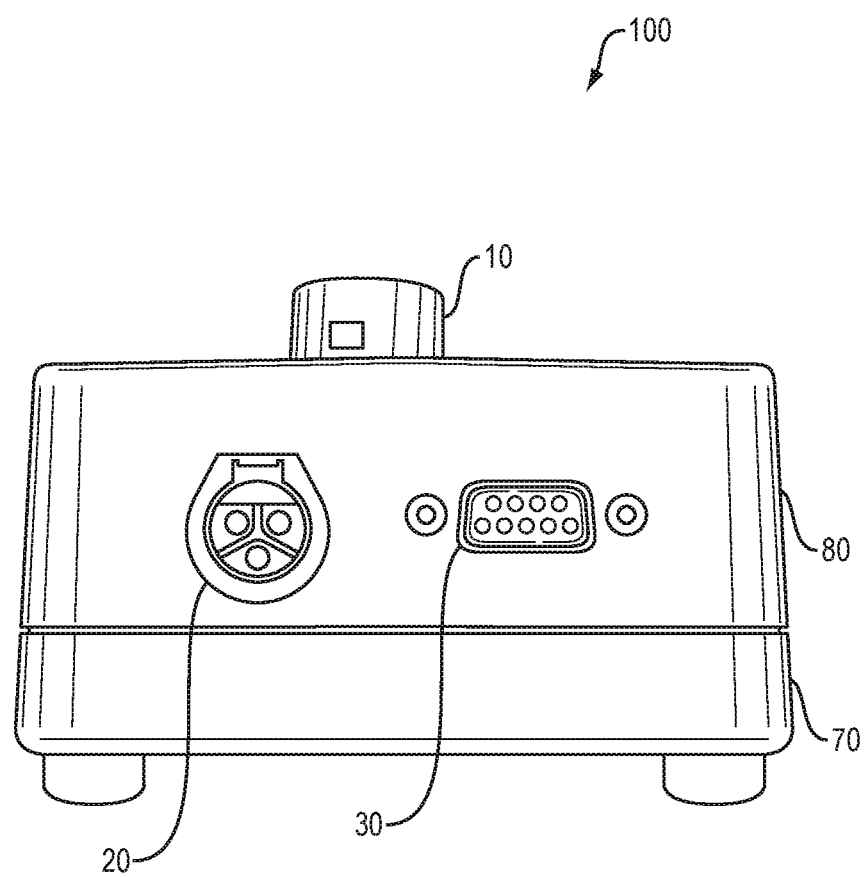
FIG. 2 is a schematic illustration of one side of the power pack as shown in FIG. 1.
Figure 3:
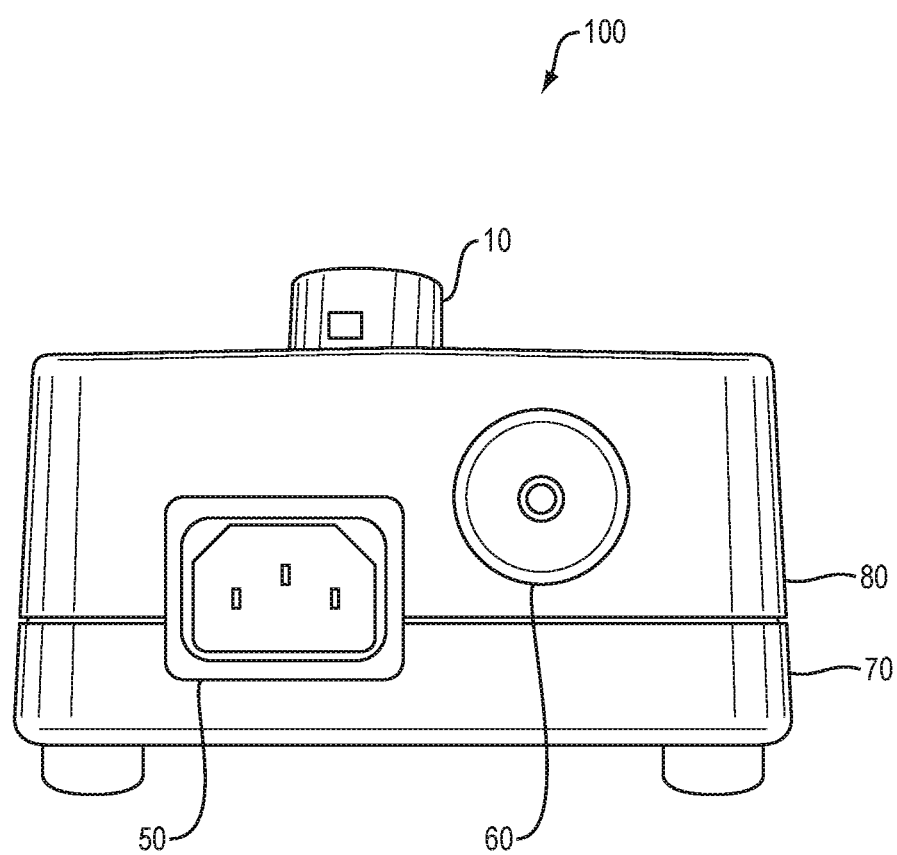
FIG. 3 is a schematic illustration of the opposite side of the power pack as shown in FIG. 1.

FIG. 1, FIG. 2, and FIG. 3 schematically illustrate a power pack from different angles or perspectives in accordance with one aspect of the present disclosure. FIG. 1 illustrates a power pack 100 with a medical device connector 10, a footswitch connector 20, a suction console connector 30, and a connection signal light or indicator 40. A side view of the power pack 100 as shown in FIG. 2 more clearly shows the medical device connector 10, the footswitch connector 20, the suction console connector 30, a base or bottom 70, and a cover or top 80. Another side view of the power pack 100 as shown in FIG. 3 further illustrates the medical device connector 10, an AC outside source connector 50, and a ground bond test or testing connector 60. It should be understood that the specific locations of the medical device connector 10, the footswitch connector 20, the suction console connector 30, the connection signal light 40, and the AC outside source connector 50 may all vary so long as they do not interfere with each other's intended functions.

Figure 4:
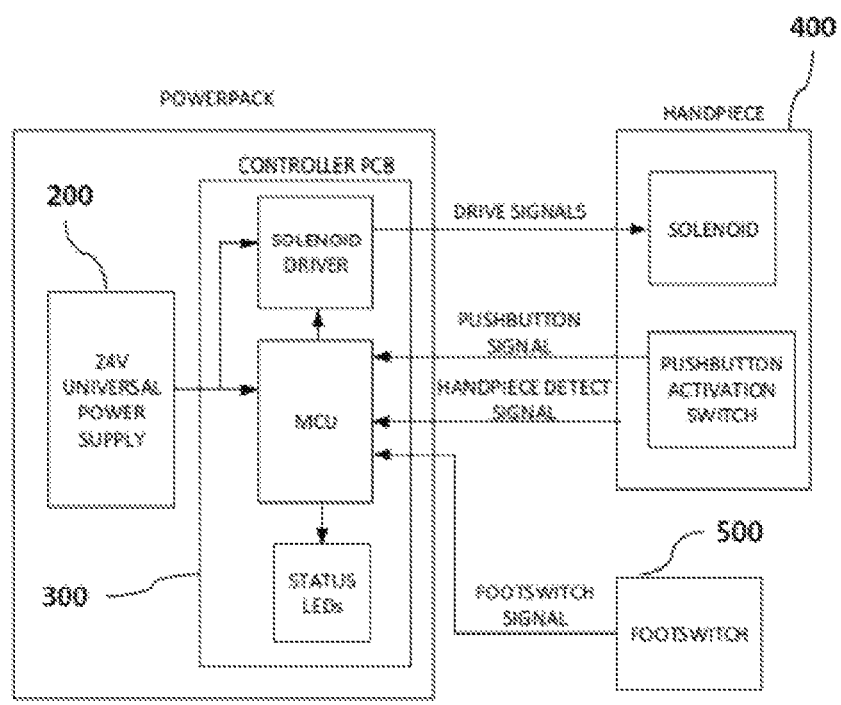
FIG. 4 is a block diagram illustrating the interactions of a controlling unit of the power pack as described herein with other components in accordance with one aspect of the present disclosure.

FIG. 4 is a block diagram illustrating one aspect as to how a controlling unit of the power pack as described herein electronically interacts with a handpiece of a medical device and with a footswitch. It should be understood that the block diagram may be similarly used or adapted for the interactions of the controlling unit of the power pack with the other accessories as described herein or known in the art.

For simplicity, the controlling unit of the power pack generally comprises a controller PCB 300 which in turn comprises a microcontroller or microcontrolling unit (MCU) and a medical device drive circuit board. It should be understood that more printed circuit boards may be necessary or desirable in order to accommodate different operational needs. The medical device drive circuit board is configured to deliver drive signals to the handpiece 400 of a medical device. The medical device drive circuit board may be a MOSFET drive circuit board. Even though FIG. 4 shows a solenoid driver sending drive signals to a solenoid disposed inside the handpiece 400, it should be understood that other medical device drivers may be similarly used to send drive signals to a variety of medical devices with different driving mechanisms. Regardless, a MOSFET drive circuit may be used under all these situations. With respect to the MCU of the controller PCB 300, it is configured among other functions to monitor the system status, to process user inputs, and to generate drive signals to control the medical device drive circuit board.

First, when a handpiece 400 of a medical device is inserted into the power pack as described herein, the controller PCB 300 is capable of generating and demonstrating a connection signal through a signal light disposed on the power pack. More particularly, the controller PCB 300 of the power pack is configured to be able of determining a particular type of handpiece through a cable employed to connect the handpiece with the power pack. More particularly, the cable is configured to utilize a combination of connections or jumpers to particular pins of the cable to represent the particular type of a handpiece. The cable may be configured to be either connected to ground or to a +5 volt. The controller PCB 300 is thus capable of identifying the type of the handpiece through identifying the specific combinations from the inserted cable of the handpiece. Even more particularly, the controller PCB 300 may be configured to be capable of identifying a handpiece having a 2 mm or 4 mm tubing for the type of the cutting blades of the medical device through the connecting cable. It may also be configured to be able of identifying other information such as driving mechanism and driving element of the medical device through the cable. It should be understood that the cable is preferably made an integral part of the handpiece or the medical device even though an independent or separate cable is also contemplated.

Furthermore, FIG. 4 shows that the controller PCB 300 receives an input signal such as a push from an activation switch or a push button located on the handpiece 400 of the medical device or a foot press from a footswitch 500, and subsequently generates an output to control the movement of the cutting blade of the medical device. Even more specifically, the controller PCB 300 may generate an output to control the reciprocating motion of the cutting blade driven by a solenoid disposed inside the handpiece of the medical device. The output may be in the form of pulse or pulse with modulation. The pulse may be in about 15 milliseconds width. The solenoid is powered by the 24V universal power supply 200, which in turn gets its power supply from an outside AC power source through a rectification and filtering unit of the power pack. The push button of the medical device may also be configured to possess a toggle function: meaning a momentary press of the push button opens and closes the cutting window or the cutting blade in the alternative. Similarly, the footswitch 500 may also be configured to have a toggle function: a momentary press of a foot pedal of the footswitch opens and closes the cutting window or the cutting blade in the alternative. Regardless, the footswitch and the push button are configured to function in a complimentary/identical fashion except when the footswitch is used with an analog output to vary the speed of the device. The controller PCB 300 is also configured to monitor and detect when a medical device is connected to the power pack. Once detected, it generates a control signal through a status LED or a signal indicator located on the exterior of the power pack. For example, the signal light or indicator may be configured to turn green from amber if a medical device is detected to be connected to the power pack. It should be understood that other type of communication/indication should also be contemplated so long as the communication/indication is clearly defined as a connection. For example, it may be a beeping sound to indicate a connection.

Additionally, when a footswitch 500 is connected to the power pack, an operator may choose between a footswitch and a push button to turn on the medical device to perform a surgical operation at his preference or convenience. If both of his hands are occupied, he may still be able to perform an operation conveniently with the footswitch. Once a push button or footswitch is activated, the MCU will then instruct the universal power supply to provide power to the medical device driver to drive the medical device to perform the desired operation. More particularly, the MCU will instruct the 24V universal power supply to power the solenoid driver to drive the solenoid to reciprocate a cutting blade to perform cutting as shown in FIG. 4.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed:

1. A power pack for a medical device having a handpiece, the power pack comprising:
   an AC power connector configured to be connectable to an outside AC power source;
   a rectification and filtering unit configured to be in electronic communication with the AC power connector;
   a controlling unit, where the controlling unit comprises a solenoid driver;
   and
   a medical device connector configured to be connectable to the medical device through a connecting cable extending from the medical device connector to the medical device, the medical device connector configured to be in electronic communication with the controlling unit,
   wherein the solenoid driver is configured to transmit a solenoid drive signal to a solenoid of the medical device, where the solenoid drive signal is configured to cause the solenoid to reciprocate a cutting blade of the medical device, where the solenoid drive signal is configured to control reciprocating motion by the solenoid of the cutting blade, and wherein the power pack is configured to provide DC power supply for the medical device at a voltage of from 12V to 36V to power the solenoid driver to drive the solenoid to reciprocate the cutting blade to perform cutting;
   the controlling unit being configured to:
      detect a connection of the medical device to the medical device connector;
      distinguish between different cutting blade types of the cutting blade; and
      determine a type of the handpiece of the medical device, wherein the controlling unit detects the connection, distinguishes between different cutting blade types, and determines the type of the handpiece through identifying a combination of connections or jumpers to particular pins of the connecting cable connecting the medical device to the power pack, and
   wherein the controlling unit is operable to adjust the solenoid drive signal to different parameters for each respective cutting blade type identified by the controlling unit to thereby optimize performance of the cutting by the cutting blade.

2. The power pack of claim 1, wherein the power pack also comprises a footswitch connector, a suction console connector, and a ground bond test connector.

3. The power pack of claim 1 where the solenoid drive signal comprises pulses or pulse width modulation (PWM).

4. The power pack of claim 3 where a drive pulse width of the solenoid drive signal comprises a range of about 5 to 25 milliseconds.

5. The power pack of claim 3 where the solenoid drive signal is configured to provide a blade reciprocation frequency of the cutting blade in a range of about 1 to about 20 hertz.

6. The power pack of claim 1 where the controlling unit is configured to adjust the solenoid drive signal to adjust a drive pulse width of the solenoid drive signal and/or a blade reciprocation frequency of reciprocation of the cutting blade of the medical device.

7. The power pack of claim 1 where the power pack comprises a single electrical connector for the medical device which the connecting cable is configured to connect to.

8. The power pack of claim 1 where the controlling unit is configured to send a signal to the solenoid to generate a toggle function to alternatively toggle open or toggle close a cutting window of the medical device based upon a user momentarily pressing a button on the medical device or a footswitch connected to the power pack.

9. The power pack of claim 1 where the solenoid driver is configured to generate the solenoid drive signal to cause the solenoid to provide a non-oscillating motion of the cutting blade of the medical device.

10. The power pack of claim 1 where the solenoid driver comprises a metal-oxide-semiconductor field-effect transistor (MOSFET) circuit.

11. A power pack for a medical device having a handpiece, the power pack comprising:
    an AC power connector configured to be connectable to an outside AC power source;
    a rectification and filtering unit configured to be in electronic communication with the AC power connector;
    a controlling unit comprising a solenoid driver;
    a medical device connector configured to be connectable to the medical device through a connecting cable extending from the medical device connector to the medical device, the medical device connector configured to be in electronic communication with the controlling unit; and
    a footswitch connector configured to be in electronic communication with the controlling unit, wherein the solenoid driver is configured to transmit a solenoid drive signal to a solenoid of the medical device, where the solenoid drive signal is configured to drive the solenoid for the solenoid to reciprocate and/or oscillate a cutting blade of the medical device, and wherein the power pack is configured to provide DC power supply for the medical device at a voltage of from 12V to 36V to power the solenoid driver to drive the solenoid to reciprocate the cutting blade to perform cutting;

the controlling unit being configured to:
  detect a connection of the medical device to the medical device connector;
  distinguish between different cutting blade types of the cutting blade; and
  determine a type of the handpiece of the medical device, wherein the controlling unit detects the connection, distinguishes between different cutting blade types, and determines the type of the handpiece through identifying a combination of connections or jumpers to particular pins of the connecting cable connecting the medical device to the power pack, and
wherein the controlling unit is further configured to send a signal to the solenoid to generate a toggle function to alternatively toggle open or toggle close a cutting window of the medical device based upon a user momentarily pressing a footswitch connected to the footswitch connector.

12. The power pack of claim 11, wherein the power pack also comprises a suction console connector, and a ground bond test connector.

13. A power pack for a medical device having a handpiece, the power pack comprising:
  a housing having an exterior;
  an AC power connector disposed on the housing, the AC power connector configured to be connectable to an outside AC power source;
  a rectification and filtering unit disposed inside the housing, the rectification and filtering unit configured to be in electronic communication with the AC power connector;
  a controlling unit disposed inside the housing, where the controlling unit comprises a solenoid driver; and
  a medical device connector disposed on the housing, the medical device connector configured to be connectable with the medical device through a connecting cable extending from the medical device connector to the medical device, wherein the solenoid driver is configured to transmit a solenoid drive signal to a solenoid of the medical device, where the solenoid driver comprises a metal-oxide-semiconductor field-effect transistor (MOSFET) circuit, where the solenoid drive signal is configured to drive the solenoid for the solenoid to reciprocate a cutting blade of the medical device, and wherein the power pack is configured to provide DC power supply for the medical device at a voltage of from 12V to 36V to power the solenoid driver to drive the solenoid to reciprocate the cutting blade to perform cutting;

the controlling unit being configured to:
  detect a connection of the medical device to the medical device connector;
  distinguish between different cutting blade types of the cutting blade; and
  determine a type of the handpiece of the medical device, wherein the controlling unit detects the connection, distinguishes between different cutting blade types, and determines the type of the handpiece through identifying a combination of connections or jumpers to particular pins of the connecting cable, where the power pack comprises a single electrical connector for the medical device, and where the controlling unit is configured to accomplish the identifying with use of the single electrical connector, and
wherein the controlling unit is configured to adjust the solenoid drive signal to different parameters for each respective cutting blade type based upon the identifying through the connecting cable and the single electrical connector.

14. The power pack of claim 13, wherein the power pack also comprises a footswitch connector in electronic communication with the controlling unit, where the controlling unit is configured to send a signal to the solenoid to generates a toggle function to alternatively toggle open or toggle close a cutting window of the medical device based upon a user momentary pressing a footswitch connected to the footswitch connector.

15. The power pack of claim 13, wherein the power pack also comprises a ground bond test connector disposed on the housing.

16. The power pack of claim 13 where the controlling unit is configured to adjust the solenoid drive signal to adjust a drive pulse width of the solenoid drive signal and/or a blade reciprocation frequency of reciprocation of the cutting blade of the medical device.

* * * * *

UNITED STATES PATENT AND TRADEMARK OFFICE
CERTIFICATE OF CORRECTION

PATENT NO. : 11,189,979 B2  
APPLICATION NO. : 16/016796  
DATED : November 30, 2021  
INVENTOR(S) : Willhite et al.

It is certified that error appears in the above-identified patent and that said Letters Patent is hereby corrected as shown below:

In the Claims

In Column 11, Line 49, in Claim 1, after "driver;", delete a linebreak

In Column 13, Line 44, in Claim 13, after "driver;", delete a linebreak

Signed and Sealed this  
Twenty-second Day of March, 2022

Drew Hirshfeld  
*Performing the Functions and Duties of the*  
*Under Secretary of Commerce for Intellectual Property and*  
*Director of the United States Patent and Trademark Office*